United States Patent
Barbagli et al.

(10) Patent No.: US 12,138,012 B2
(45) Date of Patent: *Nov. 12, 2024

(54) SYSTEMS AND METHODS FOR MEDICAL PROCEDURES USING OPTICAL COHERENCE TOMOGRAPHY SENSING

(71) Applicant: INTUITIVE SURGICAL OPERATIONS, INC., Sunnyvale, CA (US)

(72) Inventors: Federico Barbagli, San Francisco, CA (US); Christopher R. Carlson, Belmont, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 22 days.

This patent is subject to a terminal disclaimer.

(21) Appl. No.: 17/894,849

(22) Filed: Aug. 24, 2022

(65) Prior Publication Data

US 2023/0000354 A1 Jan. 5, 2023

Related U.S. Application Data

(63) Continuation of application No. 16/491,023, filed as application No. PCT/US2018/022015 on Mar. 12, 2018, now Pat. No. 11,464,411.

(Continued)

(51) Int. Cl.
*A61B 5/00* (2006.01)
*A61B 10/04* (2006.01)
(Continued)

(52) U.S. Cl.
CPC .......... *A61B 5/0036* (2018.08); *A61B 5/0066* (2013.01); *A61B 5/0084* (2013.01);
(Continued)

(58) Field of Classification Search
CPC .................................................... A61B 5/0036
See application file for complete search history.

(56) References Cited

U.S. PATENT DOCUMENTS 6,380,732 B1 4/2002 Gilboa
6,389,187 B1 5/2002 Greenaway et al.
(Continued)

FOREIGN PATENT DOCUMENTS

CN 103079478 A 5/2013
CN 105208958 A 12/2015
(Continued)

OTHER PUBLICATIONS

Extended European Search Report for Application No. EP18767446.0 mailed on Nov. 24, 2020, 7 pages.
(Continued)

*Primary Examiner* — Joseph M Santos Rodriguez
(74) *Attorney, Agent, or Firm* — Haynes & Boone, LLP.

(57) ABSTRACT

A system for performing a minimally invasive procedure includes a flexible catheter, an elongate instrument, an optical coherence tomographic sensor, and a control system. The flexible catheter has a lumen extending therethrough. The elongate instrument is sized for passage through the lumen. The optical coherence tomographic sensor is coupled to the elongate instrument. The control system includes one or more processors and is configured to receive sensor data from the optical coherence tomographic sensor, profile a tissue based on the received sensor data, and determine a distance between the elongate instrument and the profiled tissue.

20 Claims, 5 Drawing Sheets

Related U.S. Application Data (60) Provisional application No. 62/470,540, filed on Mar. 13, 2017.

(51) Int. Cl.
| | | |
|---|---|---|
| *A61B 34/37* | (2016.01) | |
| *A61B 17/00* | (2006.01) | |
| *A61B 34/30* | (2016.01) | |
| *A61B 90/00* | (2016.01) | |
| *A61M 25/01* | (2006.01) | |

(52) U.S. Cl.
CPC .............. *A61B 10/04* (2013.01); *A61B 34/37* (2016.02); *A61B 2010/045* (2013.01); *A61B 2017/00119* (2013.01); *A61B 2034/302* (2016.02); *A61B 2090/3735* (2016.02); *A61M 25/0102* (2013.01)

(56) References Cited

U.S. PATENT DOCUMENTS

| | | |
|---|---|---|
| 7,316,681 B2 | 1/2008 | Madhani et al. |
| 7,772,541 B2 | 8/2010 | Froggatt et al. |
| 8,900,131 B2 | 12/2014 | Chopra et al. |
| 9,259,274 B2 | 2/2016 | Prisco |
| 9,452,276 B2 | 9/2016 | Duindam et al. |
| 2005/0027199 A1 | 2/2005 | Clarke |
| 2006/0013523 A1 | 1/2006 | Childlers et al. |
| 2007/0077045 A1 | 4/2007 | Kato |
| 2007/0197874 A1 | 8/2007 | Ishihara |
| 2009/0234223 A1 | 9/2009 | Onoda et al. |
| 2012/0063644 A1 | 3/2012 | Popovic et al. |
| 2014/0081126 A1 | 3/2014 | Kim et al. |
| 2014/0276020 A1 | 9/2014 | Hutchins et al. |
| 2015/0141801 A1 | 5/2015 | Jean et al. |
| 2016/0374562 A1 | 12/2016 | Vertikov |
| 2020/0008678 A1 | 1/2020 | Barbagli et al. |

FOREIGN PATENT DOCUMENTS

| | | |
|---|---|---|
| JP | 2005237827 A | 9/2005 |
| JP | 2015528352 A | 9/2015 |
| WO | WO-2012040297 A2 | 3/2012 |
| WO | WO-2014053026 A1 | 4/2014 |
| WO | WO-2014121268 A1 | 8/2014 |
| WO | WO-2014139022 A1 | 9/2014 |
| WO | WO-2015054243 A1 | 4/2015 |
| WO | WO-2015089372 A1 | 6/2015 |

OTHER PUBLICATIONS

International Preliminary Report on Patentability for Application No. PCT/US2018/022015, mailed on Sep. 26, 2019, 9 pages.

International Search Report and Written Opinion for Application No. PCT/US2018/022015, mailed on Jun. 11, 2018, 12 pages.

Thiberville L., et al., "Bronchoscopic Advances: On the Way to the Cells," Respiration, 2010, vol. 79 (6), pp. 441-449.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

Office Action for Chinese Application No. CN201880007985.7, mailed Aug. 8, 2023, 35 pages.

Office Action for Chinese Application No. CN20188007985, mailed Oct. 11, 2022, 39 pages.

SYSTEMS AND METHODS FOR MEDICAL PROCEDURES USING OPTICAL COHERENCE TOMOGRAPHY SENSING

CROSS-REFERENCE TO RELATED APPLICATIONS

This patent application is a continuation of U.S. patent application Ser. No. 16/491,023 filed Sep. 4, 2019, which is the U.S. national phase of International Application No. PCT/US2018/022015, filed Mar. 12, 2018, which designated the U.S. and claims priority to and benefit of the filing date of U.S. Provisional Patent Application 62/470,540, entitled "SYSTEMS AND METHODS FOR TELEOPERATIONAL PROCEDURES USING OPTICAL COHERENCE TOMOGRAPHY SENSING," filed Mar. 13, 2017, all of which are hereby incorporated by reference in their entireties.

FIELD

The present disclosure is directed to systems and methods for performing a robotic medical procedure and more particularly to systems and methods for using optical coherence tomography (OCT) sensing to supplement a robotic medical procedure.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions physician may insert minimally invasive medical instruments (including surgical, diagnostic, therapeutic, or biopsy instruments) to reach a target tissue location. One such minimally invasive technique is to use a flexible and/or steerable elongate device, such as a flexible catheter, that can be inserted into anatomic passageways and navigated toward a region of interest within the patient anatomy. Flexible instruments may be inserted through the catheter to perform procedures at the target location. To prevent injury, certain types of tissues such as blood vessels, pulmonary pleura, and cardiac tissue should be avoided being punctured when deploying the flexible instruments. Supplemental sensing systems may be used to conduct more accurate procedures.

SUMMARY

The embodiments of the invention are best summarized by the claims that follow the description.

Consistent with some embodiments, a system for performing a minimally invasive procedure may include a flexible catheter with a lumen extending therethrough, an elongate instrument sized for passage through the lumen, and an optical coherence tomographic sensor coupled to the elongate instrument. The system may also include a control system including one or more processors. The control system may be configured to, receive sensor data from the optical coherence tomographic sensor, profile a tissue based on the received sensor data, generate an output signal based on the profiled tissue; and based on receipt of the output signal, determine a distance between the elongate instrument and the profiled tissue.

In some aspects, the elongate instrument is a biopsy needle or a removable stylet. In some aspects, the system may include a biopsy needle, and the elongate instrument may be a stylet positioned within the biopsy needle. Some aspects of the system include an alert system that provides an indicator to a user based on the distance between the elongate instrument and the profiled tissue. The indicator may comprise a notification to alter movement of the elongate instrument including at least one of reducing a velocity of the elongate instrument, suspending advancement of the elongate instrument, and retracting the elongate instrument. In some aspects, the control system is further configured to compare the determined distance to a predetermined distance limit. In some aspects, the system may include a drive system operable to control motion of the elongate instrument, wherein the control system provides a command to the drive system based on the comparison of the determined distance with the predetermined distance limit. The command may include reducing a velocity of the elongate instrument, suspending advancement of the elongate instrument, or retracting the elongate instrument. In some aspects, the control system is further configured to provide confirmation that the elongate instrument has contacted the profiled tissue. In some aspects, the system may include a display device, and the output signal is used to generate an image of the profiled tissue and an indicator of the distance between the elongate instrument and the profiled tissue to display on the display device. In some aspects, the system may include a navigation system operable to provide guidance to navigate the flexible catheter or the elongate instrument along a predefined route, and receipt of the output signal causes suspension of the advancement of the flexible catheter and elongate instrument along the predefined route. In some aspects, the profiled tissue is at least one of pulmonary pleura tissue, pulmonary fissure tissue, and blood vessel tissue. In some aspects, the system may include based on the output signal, updating a registration between an anatomic model and the elongate instrument.

Consistent with some embodiments, a method may include a method may include receiving sensor data from an optical coherence tomographic (OCT) sensor, the OCT sensor coupled to an elongate instrument. The method also may include profiling a tissue based on the received sensor data, generating an output signal based on the profiled tissue, and based on receipt of the output signal, determining a distance between the elongate instrument and the profiled tissue.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
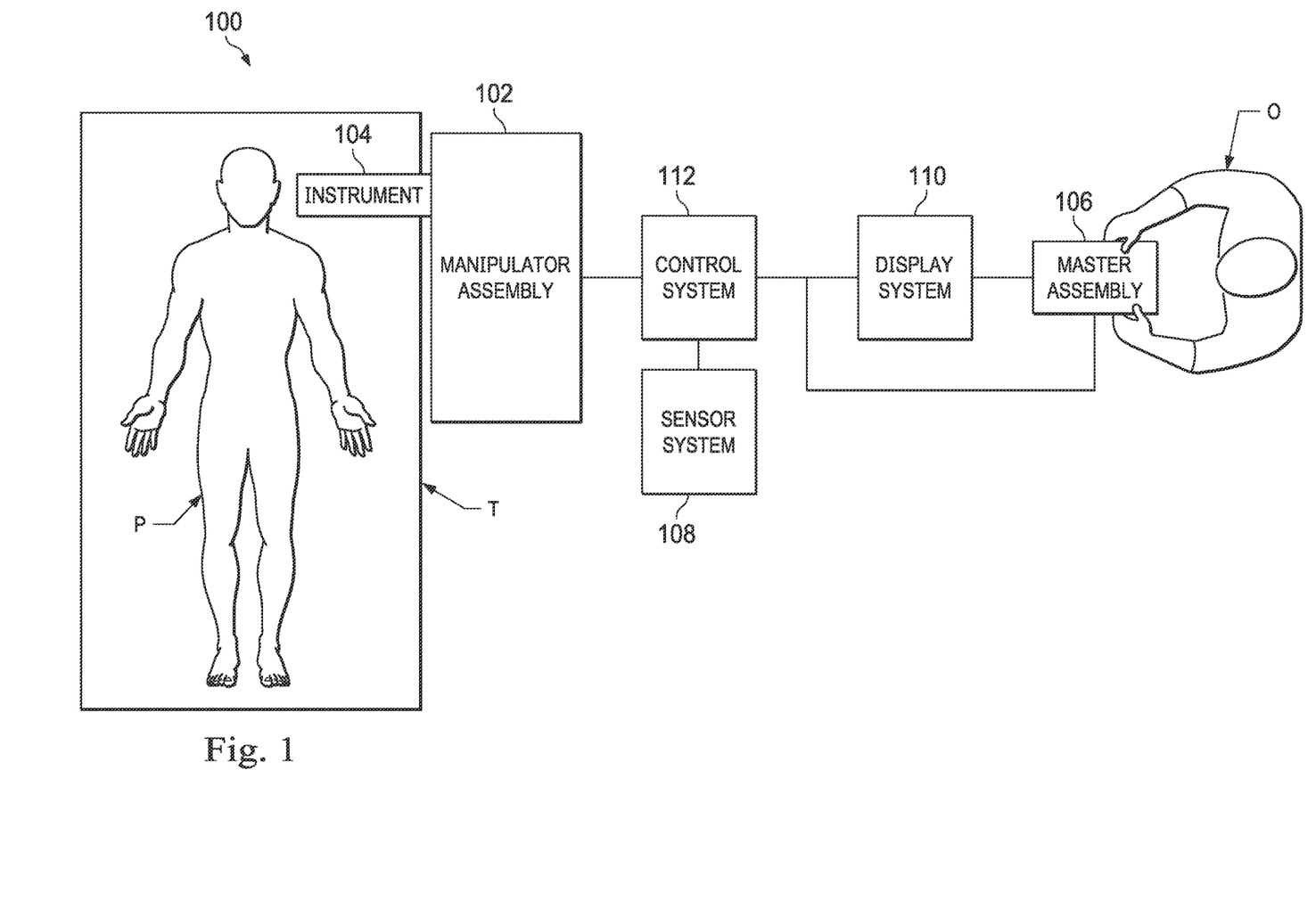
FIG. 1 is a simplified diagram of a teleoperated medical system according to some embodiments.

FIG. 1 is a simplified diagram of a teleoperated medical system 100 according to some embodiments. In some embodiments, teleoperated medical system 100 may be suitable for use in, for example, medical, surgical, diagnostic, therapeutic, or biopsy procedures. In some examples, teleoperated, medical system may operate in a non-teleoperational manner under non-teleoperator control. As shown in FIG. 1, medical system 100 generally includes a manipulator assembly 102 for operating a medical instrument 104 in performing various procedures on a patient P. Manipulator assembly 102 is mounted to or near an operating table T.

A master assembly 106 allows an operator O (e.g., a surgeon, a clinician, or a physician as illustrated in FIG. 1) to view the interventional site and to control manipulator assembly 102.

Master assembly 106 may be located at an operator's console which is usually located in the same room as operating table T, such as at the side of a surgical table on which patient P is located. However, it should be understood that operator O can be located in a different room or a completely different building from patient P. Master assembly 106 generally includes one or more control devices for controlling manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Manipulator assembly 102 supports medical instrument 104 and may include a kinematic structure of one or more non-servo controlled links (e.g., one or more links that may be manually positioned and locked in place, generally referred to as a set-up structure), a teleoperated kinematic structure, and/or a teleoperational manipulator. Manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by subsystems of sensor system 108. Display system 110 and master assembly 106 may be oriented so operator O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. The visualization system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of operator O. In this manner operator O can manipulate medical instrument 104 and the hand control as if viewing the workspace in substantially true presence. By true presence, it is meant that the presentation of an image is a true perspective image simulating the viewpoint of an operator that is physically manipulating medical instrument 104.

In some examples, display system 110 may present images of a surgical site recorded pre-operatively or intraoperatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of imaged guided surgical procedures, display system 110 may display a virtual navigational image in which the actual location of medical instrument 104 is registered (i.e., dynamically referenced) with the preoperative or concurrent images/model. This may be done to present the operator O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist operator O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist operator O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions operable to provide information to display system 110. While control system 112 is shown as a single block in the simplified schematic of FIG. 1, the system may include two or more data processing circuits with one portion of the processing optionally being performed on or adjacent to manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, manipulator assembly 102. In some embodiments, the one or more actuators and manipulator assembly 102 are provided as part of a teleoperational cart positioned adjacent to patient P and operating table T.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images. U.S. patent application Ser. No. 13/107,562 (filed May 13, 2011) (disclosing "Medical System Providing Dynamic Registration of a Model of an Anatomic Structure for Image-Guided Surgery") and International Application No. PCT/US2016/033596 (filed May 20, 2016) (disclosing "Systems And Methods Of Registration For Image Guided Surgery"), which are incorporated by reference herein in their entirety, may teach systems that register and display a medical implement together with preoperatively recorded surgical images, such as those from a virtual visualization system. Teleoperated medical system 100 may further include optional operations and support systems (not shown) such as illumination systems, steering control systems, irrigation systems, and/or suction systems. In some embodiments, teleoperated medical system 100 may include more than one teleoperational manipulator assembly associated with more than one master assembly, and/or more than one non-teleoperational manipulator assembly. The exact number of teleoperational and/or non-teleoperational manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

Figures 2A, 2B:
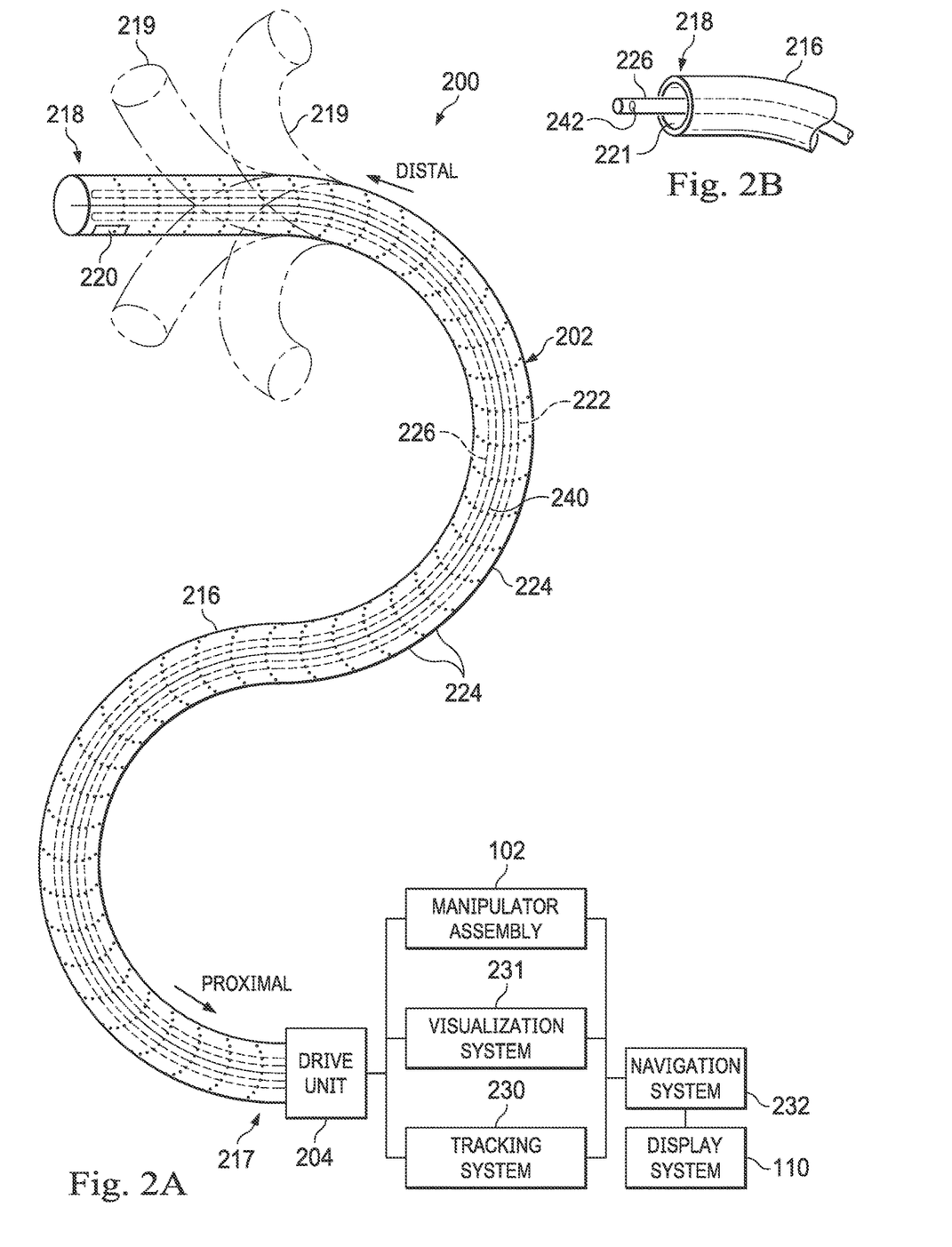
FIG. 2A is a simplified diagram of a medical instrument system according to some embodiments.
FIG. 2B is a simplified diagram of a medical instrument with an extended medical tool according to some embodiments.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

Medical instrument system 200 includes elongate device 202, such as a flexible catheter, coupled to a drive unit 204. Elongate device 202 includes a flexible body 216 having proximal end 217 and distal end or tip portion 218. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. If medical instrument system 200 is consistent with medical instrument 104 of a teleoperated medical system 100, tracking system 230. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 μm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may be a component of an EM sensor system with positional sensor system 220 including one or more conductive coils that may be subjected to an externally generated electromagnetic field. Each coil of EM sensor system 220 then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor system 220 may be positioned along flexible body 216 and then used for shape sensing. In some examples, a history of data from one or more of these sensors taken during a procedure may be used to represent the shape of elongate device 202, particularly if an anatomic passageway is generally static.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an image capture probe also within flexible body 216. In various embodiments, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

In this example, medical instrument 226 also includes an OCT imaging component 242 that provides OCT data to the visualization system 231. The OCT imaging component 242 may be a sensing component for the forward imaging of tissue distal of the medical instrument. The depth of visualization with the OCT imaging component may depend of the quality of the component and the type of tissue distal of the medical instrument 226. For example, in lung tissue, an OCT imaging component may provide visualization of tissue approximately 2-4 mm ahead of the component.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls 240 that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, manipulator assembly 102 of FIG. 1 may be replaced by direct operator control. In some examples, the direct operator control may include various handles and operator interfaces for hand-held operation of the instrument.

Figure 3A:
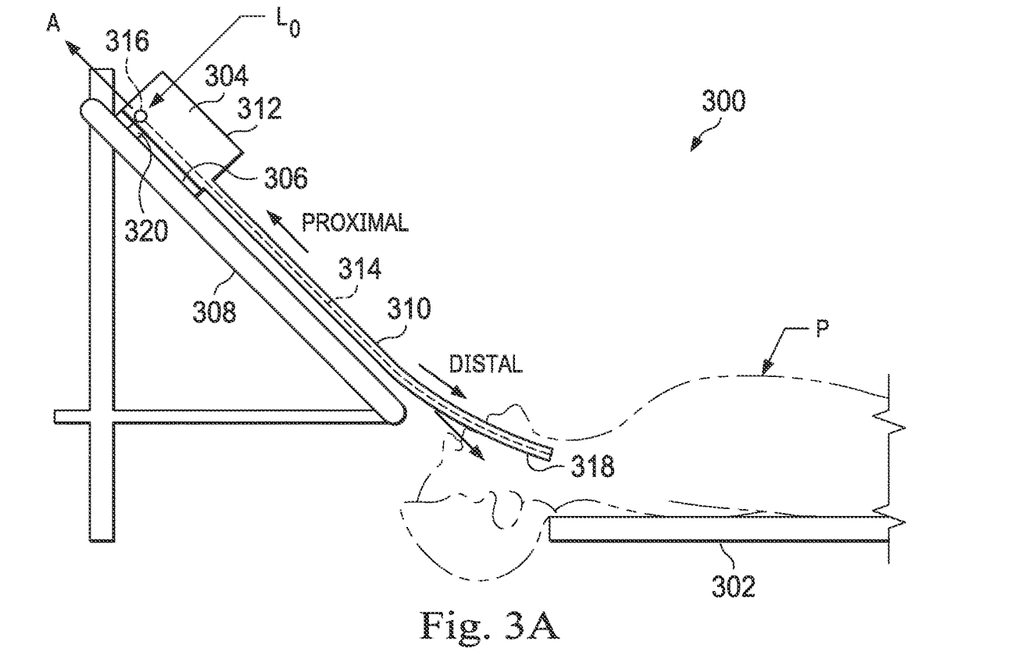
FIGS. 3A and 3B are simplified diagrams of side views of a patient coordinate space including a medical instrument mounted on an insertion assembly according to some embodiments.
Figure 3B:
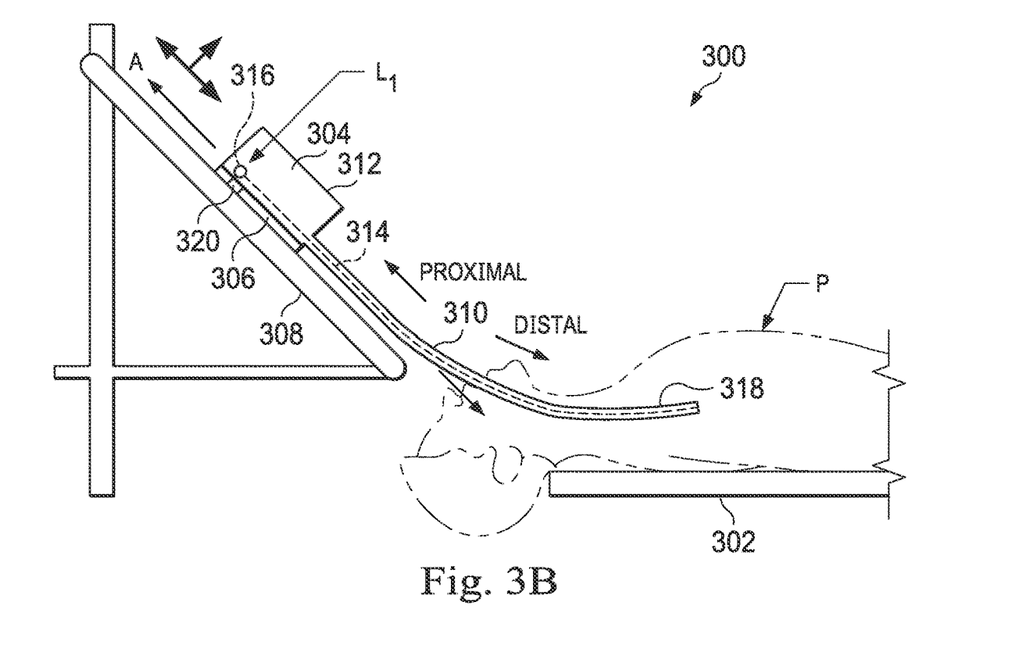

FIGS. 3A and 3B are simplified diagrams of side views of a patient coordinate space including a medical instrument mounted on an insertion assembly according to some embodiments. As shown in FIGS. 3A and 3B, a surgical environment 300 includes a patient P is positioned on platform 302. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 300, a point gathering instrument 304 is coupled to an instrument carriage 306. In some embodiments, point gathering instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a manipulator assembly (e.g., manipulator assembly 102) that couples to point gathering instrument 304 to control insertion motion (i.e., motion along the A axis) and, optionally, motion of a distal end 318 of an elongate device 310 in multiple directions including yaw, pitch, and roll. Instrument carriage 306 or insertion stage 308 may include actuators, such as servomotors, (not shown) that control motion of instrument carriage 306 along insertion stage 308.

Elongate device 310 is coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Point gathering instrument 304 may be substantially similar to medical instrument system 200.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In this retracted position, proximal point 316 is at a position $L_0$ on axis A. In this position along insertion stage 308 an A component of the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. Also in this position, position measuring device 320 may be set to a zero and/or the another reference value (e.g., I=0). In FIG. 3B, instrument body 312 and instrument carriage 306 have advanced along the linear track of insertion stage 308 and distal end 318 of elongate device 310 has advanced into patient P. In this advanced position, the proximal point 316 is at a position $L_1$ on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position $L_x$ of proximal point 316 relative to position $L_0$. In some examples, position $L_x$ may further be used as an indicator of the distance or insertion depth to which distal end 318 of elongate device 310 is inserted into the passageways of the anatomy of patient P.

A medical instrument system (e.g. system 200) may be used to display anatomic passageways and target tissue for use in virtual navigation. The target tissue may be located near sensitive tissue structures that, if inadvertently pierced, may result in a failed procedure, patient injury, or patient death. For example with a medical procedure in lung tissue, virtual navigation may be used to access target tissue in remote airways, near the boundaries of lung tissue. These passageways may be close to sensitive tissue such as visceral and parietal pleura, fissure tissue, cardiac tissue such as the aorta, vasculature including the great vessel or other blood vessels, and musculature such as the diaphragm. These types of tissue may not be visible on a navigation display, real time image, or the location of the tissue structures in the preoperatively obtained images of the navigation display may be inaccurate. This creates the risk that a deployed medical instrument may pierce the sensitive tissue. For example, if a biopsy needle pierces through the pulmonary pleura, a pneumothorax may result. Although this example generally describes the use of a medical instrument for use in the airway passageways of lung tissue, it is understood that the same systems and techniques may be applied with other types of anatomic tissue.

Real-time imaging using ultrasound, CT, and/or fluoroscopic technology may be of limited use in assisting with robotic or non-robotic medical procedures. For example, ultrasound may provide low quality images through the parenchyma due to the presence of air in the passageways of lung tissue. CT equipment may not be available in interventional pulmonology environments and may be limited in providing real-time images. Fluoroscopy equipment may be limited in the type of tissue that can be imaged or is visible in images. Both CT and fluoroscopy emit levels of radiation that may be unacceptable for extended periods of time.

OCT imaging uses reflected light energy to create three dimensional images of local tissue structures. An OCT imaging component embedded in a medical instrument may be used to generate real-time images that alone or as supplementation to other navigation images may provide more accurate tissue location information and allow the medical instrument to avoid sensitive tissue structures. An OCT imaging component or sensor may include one or more optical fiber or other tracking sensors and optical components such as lenses, couplers, and mirrors for gathering real-time OCT images and providing them to the robotic control system for analysis and display.

Figure 4:
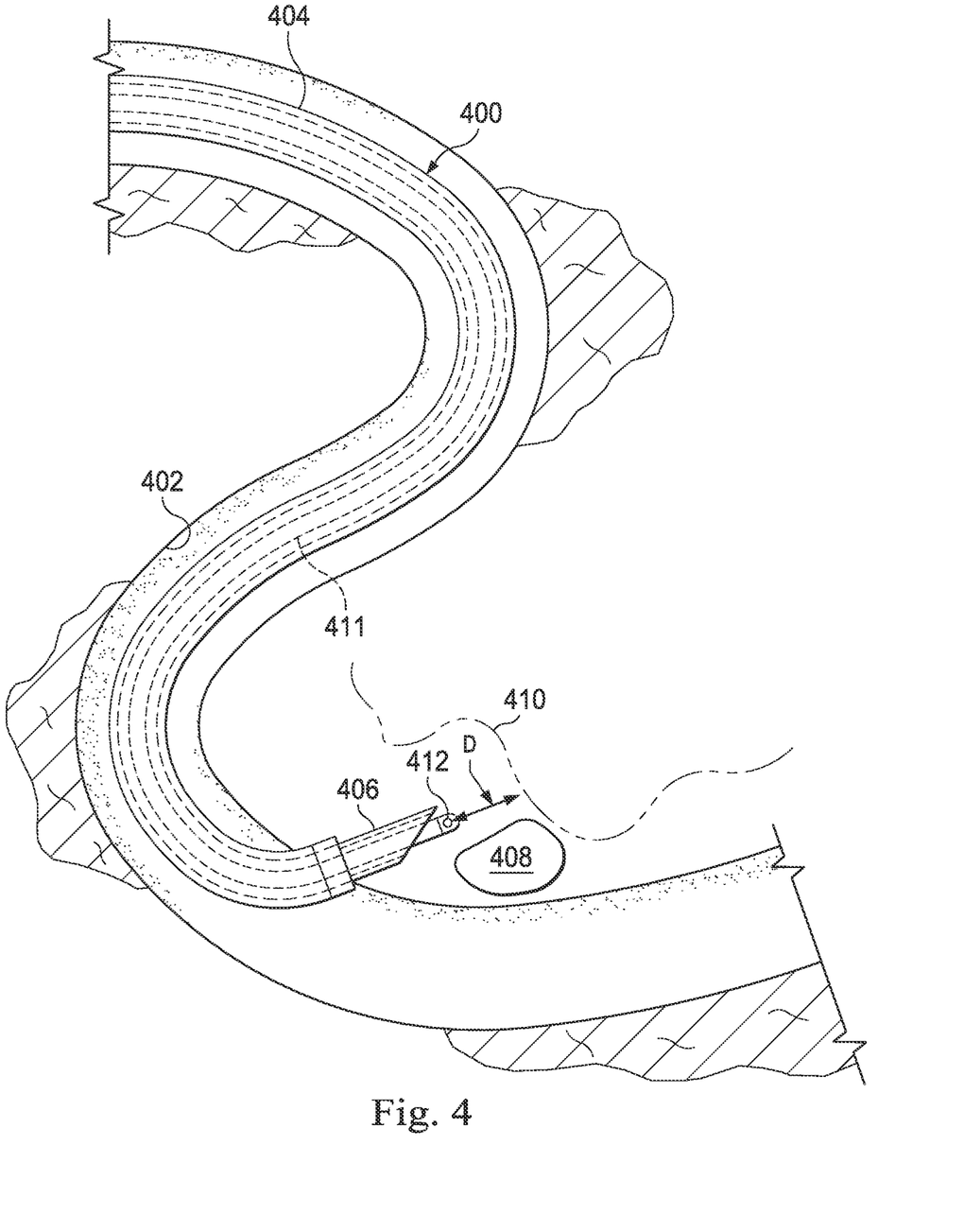
FIG. 4 illustrates a medical instrument system deployed within an anatomic passageway.

FIG. 4 illustrates a medical instrument system 400 (e.g., system 200) deployed within an anatomic passageway 402. The system 400 includes a flexible catheter 404 and a flexible instrument 406 extending through the catheter. Either one or both of the catheter 404 and the instrument 406 may be robotically or manually steerable. The system 400 may be used to conduct a medical procedure, such as a biopsy on target tissue 408. In this embodiment, target tissue 408 is outside of walls of the anatomic passageway 402 and located near sensitive tissue 410 which may be, for example, pulmonary pleura tissue. In this embodiment, the instrument 406 is a cannulated biopsy needle with a removable stylet 411 slidably extending through the biopsy needle and extendable distally of the distal end of the needle. The biopsy needle 406 may be used for sampling tissue from the target tissue 408. The stylet 411 may extend within the needle as the needle is inserted through the catheter 404 and delivered through the passageway 402 to an area near the target tissue 408. In this embodiment, the removable stylet is fitted near the distal tip with an OCT imaging component 412. In this example, the OCT imaging component may be a forward imaging component for imaging the patient anatomy and tissue distal of the instrument. Images from the OCT imaging component may be used to steer the biopsy needle toward the target tissue, avoid the sensitive tissue 410, or otherwise assist the physician in improving the accuracy and outcome of the biopsy procedure. After a desired catheter or needle depth is reached, as measured by the visualization and tracking systems alone or in combination with the OCT sensor information, the stylet may be removed. After the stylet is removed, the needle lumen is open to perform a biopsy, for example by applying suction to vacuum a tissue sample into the needle lumen. The needle may be withdrawn and the tissue sample removed and analyzed. Alternatively, with the stylet removed, the needle may be used to deliver a therapeutic substance or an ablation device.

Optionally, the control system may be used to prevent the needle from advancing distally beyond a predefined maximum insertion depth. For example, the needle may be automatically driven by the robotic system to the predefined maximum insertion depth or an alert may be provided to the controller of a manually driven needle when the predefined maximum insertion depth is reached. In a hybrid teleoperational/manual or robotic/manual system, the operator may be alerted to stop manual or teleoperational advancement of the needle when the predefined maximum insertion depth is reached.

A removable stylet with integrated OCT imaging components, may be suitable in small needle constructions because removal of the stylet and the attached OCT imaging component from the needle may allow for a minimized outer diameter of the needle and maximized inner diameter of the needle lumen. The removable stylet may be used to position multiple biopsy instruments during a single procedure, allowing the cost of the OCT enabled stylet (which may also include shape sensor or EM sensor components) to be amortized over multiple biopsy instruments.

Figure 6A:
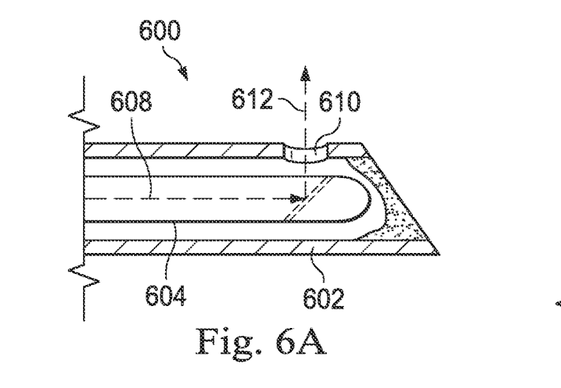
FIGS. 6A and 6B illustrate alternative distal ends of an OCT instrument.
Figure 6B:
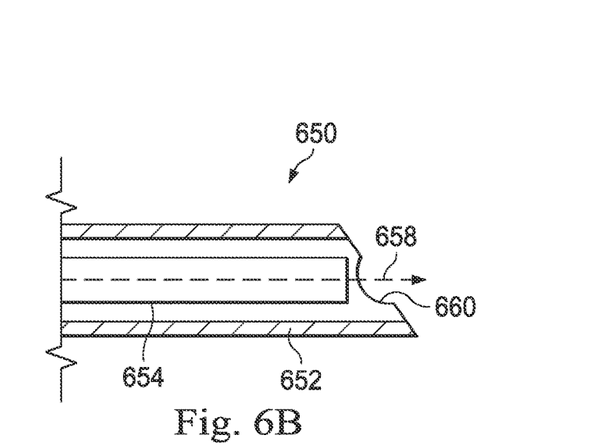

In alternative embodiments, the OCT imaging component may be fixed within the instrument 406. For example, as shown in FIG. 6A, a side-imaging OCT instrument 600 (e.g., instrument 406 or stylet 411) may include an outer wall 602 housing an optical assembly 604 which may include one or more optical fibers, lenses, filters, mirrors, or other optical components for directing a light beam 608 through a side aperture 610 in the outer wall. A light beam 612 emerging from the side aperture 610 may be used to perform the OCT imaging. In the example shown in FIG. 6B, a forward-facing OCT instrument 650 (e.g., instrument 406 or stylet 411) may include an outer wall 652 housing an optical assembly 654 which may include one or more optical fibers, lenses, filters, mirrors, or other optical components for directing a light beam 658 through a distal aperture 660. The light beam 658 emerging from the distal aperture 660 may be used to perform the OCT imaging.

Figure 5:
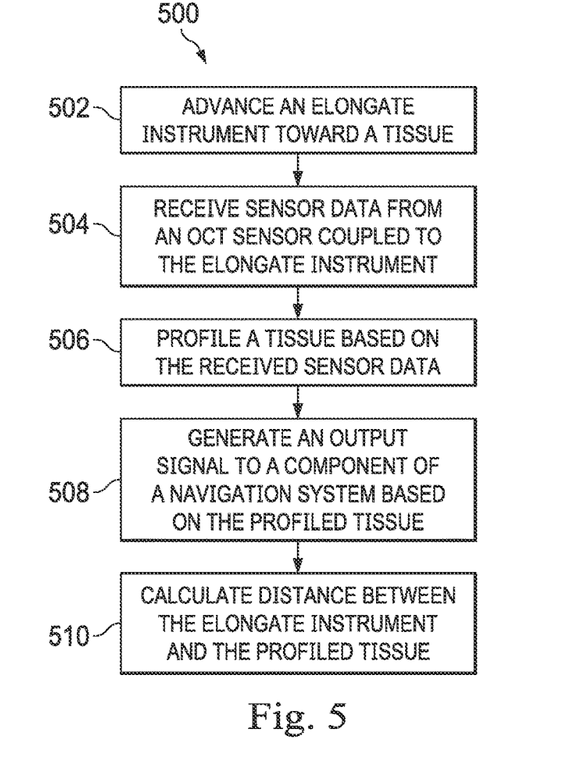
FIG. 5 illustrates a method for using OCT imaging data to profile tissue and signal a component of a teleoperational system.

In various embodiments, OCT imaging data from the instrument or stylet may be used to generate an OCT image for display to the physician for use in guiding the catheter 404 to a parking location near the target tissue 408 or for use in guiding the instrument 406 from the parked catheter 404 toward target tissue. FIG. 5 illustrates a method 500 for using OCT imaging data to profile tissue and transmit an information signal a component of a navigation system for display or navigational control. The method 500 is illustrated as a set of operations or processes 502-510. Not all of the illustrated processes 502-510 may be performed in all embodiments of method 500. Additionally, one or more processes that are not expressly illustrated in FIG. 10 may be included before, after, in between, or as part of the processes 502-506. In some embodiments, one or more of the processes 502-510 are optional and may be omitted. All or only parts of the processes 502-510 described herein may be performed with robotic control including both teleoperated control and automatic control, or may be performed with manual control.

At a process 502, the instrument 406 is advanced toward a target tissue 408. The advancement may be fully automated, teleoperationally controlled, or manually controlled. For example, the instrument 406 may advance along a route established by the navigation system. At a process 504, OCT imaging data is received from an OCT sensor (e.g. OCT imaging component 412 which may be either on the instrument or a stylet). In one example, the OCT image data is received after the catheter 404 and instrument 406 have been navigated to a park location within the anatomic passageway 402 near the target tissue 408. The OCT imaging data may be used to visualize tissue beyond the wall of the anatomic passageway 402 in the vicinity of the park location. Optionally, the OCT image data may be used to generate a real-time image for display to the physician on a display screen (e.g., display 110).

At a process 506, the OCT imaging data is processed by the control system of the teleoperational system (e.g. the control system 112) to profile the type of tissue in the OCT image data. The control system 112 may analyze the characteristics of the tissue in the OCT image data and match the characteristics with stored profiles of different types of tissue such as pleura tissue, cardiac tissue, vascular tissue, muscle tissue, bone tissue, and tumor tissue. Some types of profiled tissue may be characterized as sensitive tissue to be avoided by medical instruments.

At a process 508, the navigation system uses the profile of the imaged tissue to assist the physician with subsequent steps in the medical procedure using the instrument 406. One or more output information signals may be generated by the control system 112 based on the profile of the imaged tissue. The output information signal may, for example, provide information about the profiled tissue, the location of the profiled tissue, and/or the position of the profiled tissue relative to other tissues. The output signal may be sent to the navigation system, the display system, the drive system, an/or other components of the teleoperational or robotic system.

At a process 510, if the imaged tissue includes tissue profiled as sensitive tissue 410, a distance D between the imaging component 412 and the sensitive tissue 410 may be calculated. The location of the imaging component 412 may be kinematically known relative to the instrument 406. Distance D may be displayed to the physician to help the physician avoid moving the instrument 406 into contact with the tissue 410. The control system 112 may compare the distance D to a predefined safety distance and issue an auditory or visual alert when the distance D becomes smaller than the predefined safety distance, indicating that the instrument 406 has advanced too close to the sensitive tissue. In various embodiments, the navigation system of the robotic system may issue commands to suspend advancement of the robotic assembly and instrument drive systems to prevent the instrument 406 from advancing closer to the sensitive tissue than the predefined safety distance. Alternatively, suspending advancement may include sending the alert to warn an operator of a manually driven or teleoperationally driven instrument to suspend further advancement of the instrument. In various embodiments, the navigation system of the robotic system may issue commands to the robotic assembly and instrument drive systems to cause the instrument 406 to retract if it meets or exceeds the predefined safety distance, or issue an alert or notification to the user to manually or teleoperationally retract the assembly a predefined or recommended safe distance.

In various embodiments, the navigation system of the robotic system may issue commands to the robotic assembly and instrument drive systems to slow the velocity of the advancing instrument 406 as it approaches the predefined safety distance. For example, the navigation system may provide information indicating that the needle is approaching sensitive tissue such as the pleura, and the receipt of that information may trigger the OCT imaging system to begin imaging or begin analyzing images to identify the sensitive tissue in the OCT image data. This additional OCT data about the location of the sensitive tissue may be used to update registration with the anatomic model. Similarly, if analysis of the OCT image data indicates that sensitive tissue is not where it was predicted to be by the navigation system, that updated information may be used to update the registration.

Alternatively, the profile of the imaged tissue may be used to confirm the accuracy of the medical procedure. For example, if the instrument is a biopsy instrument, the profile of the OCT imaged tissue may provide feedback confirming that the target tissue has been sampled or alerting the physician that the target tissue was missed. Based on this feedback, the navigation system may provide guidance to the physician to move the catheter or instrument to access the target tissue by another approach or trajectory. Using the tissue profile information, the navigation system may suggest multiple biopsy locations in the target tissue. In another alternative, the accuracy of an ablation procedure may be confirmed by analysis of OCT image data that shows the tissue shows indications of ablation.

Although the OCT image data may be useful when the catheter is parked, as described, in alternative examples, the OCT image data may be used to improve navigation while the catheter 404 and instrument 406 are advancing within the passageway 402 toward the park location. For example, OCT image data may provide real-time images of lesions within the anatomic passages for avoidance or for performing a medical procedure.

One or more elements in embodiments of the invention (e.g., the processing of signals received from the input controls and/or control of the flexible catheter) may be implemented in software to execute on a processor of a computer system, such as control system 112. When implemented in software, the elements of the embodiments of the invention are essentially the code segments to perform the necessary tasks. The program or code segments can be stored in a non-transitory machine-readable storage media, including any media that can store information including an optical medium, semiconductor medium, and magnetic medium. Machine-readable storage media examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. As described herein, operations of accessing, detecting, initiating, registered, displaying, receiving, generating, determining, moving data points, segmenting, matching, etc. may be performed at least in part by the control system 112 or the processors thereof.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:
1. A system for performing a minimally invasive procedure, the system comprising:
    a flexible catheter with a lumen extending therethrough;
    an elongate instrument sized for passage through the lumen;

an optical coherence tomographic sensor coupled to the elongate instrument; and a control system including one or more processors, wherein the control system is configured to:
receive sensor data from the optical coherence tomographic sensor;
profile a tissue based on the received sensor data; and
determine a distance between the elongate instrument and the profiled tissue.

2. The system of claim 1, wherein the elongate instrument is a biopsy needle or a removable stylet.

3. The system of claim 1, further comprising a biopsy needle sized for passage through the lumen, wherein the elongate instrument comprises a stylet sized for passage through the biopsy needle.

4. The system of claim 1, further comprising an alert system operable to provide an indicator to a user based on the distance between the elongate instrument and the profiled tissue.

5. The system of claim 4, wherein the indicator comprises a notification to alter movement of the elongate instrument including at least one of reducing a velocity of the elongate instrument, suspending advancement of the elongate instrument, or retracting the elongate instrument.

6. The system of claim 1, further comprising a drive system operable to control motion of the elongate instrument, wherein the control system provides a command to the drive system based on a comparison of the determined distance with a predetermined distance limit.

7. The system of claim 6, wherein the command includes reducing a velocity of the elongate instrument, suspending advancement of the elongate instrument, or retracting the elongate instrument.

8. The system of claim 1, further comprising a display device, wherein the control system is further configured to generate an image of the profiled tissue and an indicator of the distance between the elongate instrument and the profiled tissue to display on the display device.

9. The system of claim 1, further comprising a navigation system operable to provide guidance to navigate the flexible catheter or the elongate instrument along a predefined route, wherein receipt of the determined distance causes suspension of advancement of the flexible catheter and elongate instrument along the predefined route.

10. A method comprising:
receiving sensor data from an optical coherence tomographic (OCT) sensor, the OCT sensor coupled to an elongate instrument;
profiling a tissue based on the received sensor data; and
determining a distance between the elongate instrument and the profiled tissue.

11. The method of claim 10, further comprising displaying, on a display device, an indicator of the distance between the elongate instrument and the profiled tissue.

12. The method of claim 10, further comprising comparing the determined distance to a predetermined distance limit and altering movement of the elongate instrument based on the comparison.

13. The method of claim 12, wherein altering the movement of the elongate instrument includes at least one of suspending advancement of the elongate instrument, altering velocity of advancement of the elongate instrument, or retracting the elongate instrument.

14. The method of claim 10, further comprising providing an alert to a user based on the distance between the elongate instrument and the profiled tissue.

15. The method of claim 10, further comprising using the received sensor data to generate an image of the profiled tissue on a display device.

16. The method of claim 10, further comprising providing confirmation that the elongate instrument has contacted the profiled tissue.

17. The method of claim 10, wherein the profiled tissue is at least one of pulmonary pleura tissue, pulmonary fissure tissue, or blood vessel tissue.

18. The method of claim 10, further comprising updating a registration between an anatomic model and the elongate instrument based on the profiled tissue.

19. The method of claim 10, further comprising providing guidance to navigate the elongate instrument along a predefined route, wherein, based on the determined distance, the guidance includes a notification to alter movement of the elongate instrument including suspension of advancement of the elongate instrument along the predefined route.

20. The method of claim 10, wherein the elongate instrument comprises a stylet positioned within a biopsy needle extending through a lumen of a flexible catheter.

* * * * *